US010010533B2

(12) United States Patent
Palepu et al.

(10) Patent No.: US 10,010,533 B2
(45) Date of Patent: *Jul. 3, 2018

(54) FORMULATIONS OF BENDAMUSTINE

(71) Applicant: Eagle Pharmaceuticals, Inc., Woodcliff Lake, NJ (US)

(72) Inventors: Nagesh R. Palepu, Southampton, PA (US); Philip Christopher Buxton, Great Dunmow (GB)

(73) Assignee: EAGLE PHARMACEUTICALS, INC., Woodcliff Lake, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/432,335

(22) Filed: Feb. 14, 2017

(65) Prior Publication Data

US 2018/0000789 A1    Jan. 4, 2018

Related U.S. Application Data

(63) Continuation of application No. 15/013,436, filed on Feb. 2, 2016, now Pat. No. 9,572,797, which is a continuation of application No. 14/031,879, filed on Sep. 19, 2013, now Pat. No. 9,265,831, which is a continuation of application No. 13/016,473, filed on Jan. 28, 2011, now Pat. No. 8,609,707.

(60) Provisional application No. 61/299,100, filed on Jan. 28, 2010.

(51) Int. Cl.
*A61K 47/10* (2017.01)
*A61K 31/4184* (2006.01)
*A61K 9/08* (2006.01)
*A61K 47/20* (2006.01)
*A61K 47/12* (2006.01)
*A61K 47/22* (2006.01)
*A61K 47/18* (2017.01)
*A61K 9/00* (2006.01)

(52) U.S. Cl.
CPC ............ *A61K 31/4184* (2013.01); *A61K 9/08* (2013.01); *A61K 47/10* (2013.01); *A61K 47/12* (2013.01); *A61K 47/18* (2013.01); *A61K 47/186* (2013.01); *A61K 47/20* (2013.01); *A61K 47/22* (2013.01); *A61K 9/0019* (2013.01)

(58) Field of Classification Search
CPC .... A61K 31/4184; A61K 47/10; A61K 47/12; A61K 47/18; A61K 47/186; A61K 47/20; A61K 47/22; A61K 9/0019; A61K 9/08
See application file for complete search history.

(56) References Cited

U.S. PATENT DOCUMENTS

| | | |
|---|---|---|
| 4,071,620 A | 1/1978 | Sklar |
| 4,711,906 A | 12/1987 | Von Stetten et al. |
| 4,879,286 A | 11/1989 | Alam et al. |
| 5,223,515 A | 6/1993 | Mikura et al. |
| 7,772,274 B1 | 8/2010 | Palepu |
| 8,076,366 B2 | 12/2011 | Courvoisier et al. |
| 8,344,006 B2 | 1/2013 | Drager et al. |
| 8,389,558 B2 | 3/2013 | Alakhov et al. |
| 8,609,707 B2 | 12/2013 | Palepu et al. |
| 8,791,270 B2 | 7/2014 | Brittain et al. |
| 9,000,021 B2 | 4/2015 | Sundaram et al. |
| 9,034,908 B2 | 5/2015 | Sundaram |
| 9,144,568 B1 | 9/2015 | Sundaram |
| 9,265,831 B2 | 2/2016 | Palepu et al. |
| 9,572,796 B2 | 2/2017 | Palepu et al. |
| 9,572,797 B2 | 2/2017 | Palepu et al. |
| 9,572,887 B2 | 2/2017 | Palepu et al. |
| 9,579,384 B2 | 2/2017 | Sundaram et al. |
| 9,597,397 B2 | 3/2017 | Sundaram |
| 9,597,398 B2 | 3/2017 | Sundaram |
| 9,597,399 B2 | 3/2017 | Sundaram |
| 2004/0043069 A1 | 3/2004 | Vanderbist et al. |
| 2005/0042285 A1 | 2/2005 | Ukai et al. |
| 2006/0035945 A1 | 2/2006 | Attardo et al. |
| 2006/0128777 A1 | 6/2006 | Bendall et al. |
| 2006/0159713 A1 | 7/2006 | Brittain et al. |
| 2008/0118544 A1 | 5/2008 | Wang |
| 2009/0082416 A1 | 3/2009 | Czarnik |
| 2009/0209606 A1 | 8/2009 | Bendall et al. |
| 2009/0264488 A1 | 10/2009 | Cooper et al. |
| 2009/0325978 A1 | 12/2009 | Onai et al. |
| 2010/0092474 A1 | 4/2010 | Gallagher et al. |
| 2010/0145266 A1 | 6/2010 | Orlowski et al. |

(Continued)

FOREIGN PATENT DOCUMENTS

| | | |
|---|---|---|
| CN | 101584668 A | 11/2009 |
| CN | 102164579 A | 8/2011 |

(Continued)

OTHER PUBLICATIONS

Biewenga et al., "The Pharmacology of the Antioxidant Lipoic Acid," Gen. Pharmac., vol. 39, No. 3, pp. 315-331 (1997).

(Continued)

*Primary Examiner* — Ernst V Arnold
(74) *Attorney, Agent, or Firm* — Lucas & Mercanti, LLP

(57) ABSTRACT

Long term storage stable bendamustine-containing compositions are disclosed. The compositions can include bendamustine or a pharmaceutically acceptable salt thereof, and a pharmaceutically acceptable fluid which can include in some embodiments PEG, PG or mixtures thereof and an antioxidant or chloride ion source. The bendamustine-containing compositions have less than about 5% total impurities, on a normalized peak area response ("PAR") basis as determined by high performance liquid chromatography ("HPLC") at a wavelength of 223 nm, after at least about 15 months of storage at a temperature of from about 5° C. to about 25° C.

26 Claims, No Drawings

(56) References Cited

U.S. PATENT DOCUMENTS

| | | | |
|---|---|---|---|
| 2010/0216858 | A1 | 8/2010 | Popek et al. |
| 2010/0273730 | A1 | 10/2010 | Hsu et al. |
| 2011/0015244 | A1 | 1/2011 | Alakhov et al. |
| 2011/0015245 | A1 | 1/2011 | Alakhov et al. |
| 2011/0184036 | A1 | 7/2011 | Palepu et al. |
| 2011/0190363 | A1 | 8/2011 | Drager et al. |
| 2012/0059000 | A1 | 3/2012 | Ren et al. |
| 2012/0071532 | A1 | 3/2012 | Cooper et al. |
| 2012/0157505 | A1 | 6/2012 | La Bell et al. |
| 2013/0041003 | A1 | 2/2013 | Brittain et al. |
| 2013/0041004 | A1 | 2/2013 | Drager et al. |
| 2013/0210878 | A1 | 8/2013 | Soppimath et al. |
| 2013/0210879 | A1 | 8/2013 | Palepu et al. |
| 2013/0253025 | A1 | 9/2013 | Sundaram et al. |
| 2014/0094496 | A1 | 4/2014 | Sundaram et al. |
| 2014/0275196 | A1 | 9/2014 | Sundaram |

FOREIGN PATENT DOCUMENTS

| | | |
|---|---|---|
| DE | 159289 | 3/1983 |
| JP | H09508128 A | 8/1997 |
| JP | 2005537285 A | 12/2005 |
| JP | 2008526991 A | 7/2008 |
| JP | 2012503666 A | 2/2012 |
| JP | 2012525387 A | 10/2012 |
| JP | 2015501814 A | 1/2015 |
| WO | 9901118 A2 | 1/1999 |
| WO | 0202125 A1 | 1/2002 |
| WO | 2006054315 A1 | 5/2006 |
| WO | 2006110551 A2 | 10/2006 |
| WO | 2010036702 A1 | 4/2010 |
| WO | 2010126676 A1 | 11/2010 |
| WO | 2010148288 A2 | 12/2010 |
| WO | 2011094565 A1 | 8/2011 |
| WO | 2012015810 A2 | 2/2012 |
| WO | 2013142358 A1 | 9/2013 |

OTHER PUBLICATIONS

Rowe et al., "Handbook of Pharmaceutical Excipients," 6th edition, pp. 454-455 (2009).
Spiegel et al., "Use of Nonaqueous Solvents in Parenteral Products," Journal of Pharmaceutical Sciences, vol. 52, No. 10 pp. 917-927 (1963).
International Search Report and Written Opinion issued in counterpart PCT/US2013/26187 dated May 2013 (2 pages).
Thiesen, "Bendamustine, a well-tollerated cytotoxic agent used in Germany for may years, is soon to be marketed in the rest of Europe for a range of indicatons including chronic lymphocytic leukaemia," pp. 1-4 (2010). Available at http://www.hospitalpharmacyeurope.com/featured-articles/bendamustine.
Preiss et al., "Pharmacological and clinical date of Bendamustine," 17th International Cancer Congress, pp. 1637-1640 (1998).
Schoffski et al., "Weekly administration of bendamustine: A phase 1 study in patients with advanced progressive solid tumors," Annals of Oncology II, pp. 729-734 (2000).
Rassachaert et al., "A phase 1 study of bendamustine hydrochloride administered once every 3 weeks in patients with solid tumors," Anti-Cancer Drugs, vol. 18 No. 5 pp. 587-595 (2007).
Schoffski et al., Repeated administration of short infusions of bendamustine: a phase 1 study in patients with advanced progressive solid tumours, J. Cancer Res Clin Oncol, vol. 126 No. 1 pp. 41-47 (2000).
Treanda, "Highlights of Prescribing Information," TREANDA ( bendamustine hydrochloride) for Injection, for intravenous infusion, pp. 1-13 (2010).
Zips et al., "New Anticancer Agents: In Vitro and In Vivo Evaluation," In Vivo,vol. 19 pp. 1-8 (2005).
Sikora, "Cancer drug development in the post-genomic age," Current Science, vol. 81 No. 5 pp. 549-554 (2001).
International Search Report and Written Opinion issued in counterpart PCT/US2013/032295 dated Jun. 2013 (4 pages).
International Search Report and Written Opinion of International application based on PCT/US2011/022958, dated Apr. 2011 (8 pages).
Third Party Submission in related EP2528602 based on PCT/US2011/022958 dated Nov. 2013.
Supplementary European Search Report in related EP 2528602 dated Jan. 2014.
Maas et al., "Stabilitat von Bendamustinhydrochlorid in Infusionslosungen," DIE Pharmazie, Govi Verlag Pharmazeutischer Verlag GMBH, vol. 49. No. 10 pp. 775-777 (1994) and English translation.
International Search Report and Written Opinion for No. PCT/US2013/032289 dated Jun. 2013.
Sigma-Aldrich, Webpage Catalog for poly(ethylene glycol), http://www.sigmaaldrich.com/catalog/product/aldrich/202398?lang=en&region=US#, accessed Nov. 15, 2015 (2 pages).
W. Fürst, et al., "About the Hydrolytic Decomposition of IMET 3393," Pharmazeutische Zentralhalle, vol. 108, Issue 9, pp. 608-614, 1969 (English translation and the original article).
Michael J. Akers, "Excipient-Drug Interactions in Parentaral Formulations," Journal of Pharmaceutical Sciences, vol. 91, Issue 11, pp. 2283-2300, 2002.
Julia A. Barman Balfour, et al., "Bendamustine", Drugs, vol. 61, No. 5, pp. 631-638, 2001.
Charles P. Carpenter, et al., A Study of the Polyethylene Glycols as Vehicles . . . , Journal of the American Pharmaceutical Association, vol. XII, No. 1.
Michael P. Gamcsik, et al., NMR Studies of the Conjugation . . . , J. Med. Chem., vol. 33, pp. 1009-1014, 1990.
Michael J. Akers, Remington, The Science and Practice of Pharmacy 21st Edition,Parenteral preparation, chapter 41, pp. 802-835, 2005.
Neelam Seedher, et al., Solubilization of Nimesulide; Use of Co-solvents, Indian J. Pharm. Sci., vol. 65, No. 1, pp. 58-61, 2003.
Bernard Testa, et al., Hydrolysis in Drug and Prodrug Metabolism, pp. 681-684.
Kurt H. Bauer, et al., Pharmazeutische Technologies, pp. 424-425, HW10, 1993.
Lian-Feng Huang, et al., Water-Insoluble Drug Formulation, Second Edition, Ch. 7. Formulation Strategies and Practice . . . Support, pp. 113-132.
Larry A. Gatlin, et al., Injectable Drug Development, 17. Formulation and Administration . . . Products, pp. 401-420.
McGinity, et al., Journal of Pharmaceutical Sciences, Influence of Peroxide Impurities in Polyethylene Glycols . . . , vol. 64, No. 2 pp. 356-357, 1975.
Paul J. Sheskey, Handbook of Pharmaceutical Excipients, 7th Edition, Propyl Gallate.
Jay S. Trivedi, Water-Insoluble Drug Formulation, Second Edition, 9 Solubilization Using Cosolvent Approach, pp. 161-194, 2008.
Eric Watson, et al., Kinetics of Phosphoramide Mustard . . . , Journal of Pharmaceutical Sciences, vol. 74, No. 12, pp. 1283-1292, 1985.
Kurt H. Bauer, et al., Pharmazeutische Technologies, pp. 225-228, HW9, 1993.
Orrie M. Friedman, et al., Calorimetric Estimation of Nitrogen . . . , Analytical Chemistry, pp. 906-910.
Jay S. Trivedi, et al., Water-Insoluble Drug Formulation, 7. Solubilization Using CoSolvent Approach, pp. 141-168, 2000.
V.M Mikhal'chuk, et al., Antioxidative Stabilization of Polyethylene . . . , Russian Journal of Applied Chemistry, vol. 77, No. 1, pp. 131-135, 2004.
V.G. Vinogradova, et al., Polymer Yearbook 13, New Metal Chelates as Antioxidant Stabilizers for Polymers . . . , pp. 87-111, 1996.
E. Santacesaria, et al., Thermal Stability of Nonionic Polyoxyalkylene . . . , Journal of Applied Polymer Science, vol. 42, pp. 2053-2061, 1991.
Spectra Analysis, Inc., Oxidative Degradation of Polyethyleneglycol . . . , Application Note 016, Mar. 2008.

(56) References Cited

OTHER PUBLICATIONS

Derry E. Wilman, Application of 15N Nuclear Magnetic Resonance . . . , J. Med. Chem., vol. 38, pp. 2256-2258, 1995.
Kenneth E. Avis, et al., Remington, Parenteral Preparations, Chapter 41, pp. 780-786, 2000.
William H. Brown, Organic Chemistry 5th Edition, pp. 358-360, 2009.
Sandeep Nema, et al., Excipients and Their Use in Injectable Products, PDA Journal of Pharmaceutical Science & Technology, May 16, 1997.
JC Price, Handbook of Pharm. Excipients, 5th Edition, Polyethylene Glycol, pp. 545-550, Aug. 9, 2005.
Brigitte C. Scott, et al., Lipoic and Dihydrolipoic Acids . . . , Free Rad. Res., vol. 20, No. 2, pp. 119-133, 1994.

FORMULATIONS OF BENDAMUSTINE

CROSS-REFERENCE TO RELATED APPLICATIONS

This application is a continuation of application Ser. No. 15/013,436, filed Feb. 2, 2016 now U.S. Pat. No. 9,572,797, which is a continuation of application Ser. No. 14/031,879, filed Sep. 19, 2013, now U.S. Pat. No. 9,265,831, issued Feb. 23, 2016, which is a continuation of application Ser. No. 13/016,473, filed Jan. 28, 2011, now U.S. Pat. No. 8,609,707, issued Dec. 17, 2013, which claims the benefit of U.S. Provisional Patent Application No. 61/299,100, filed Jan. 28, 2010, the contents of each of which are incorporated herein by reference.

BACKGROUND OF THE INVENTION

Bendamustine free base is represented by the following structural formula (I)

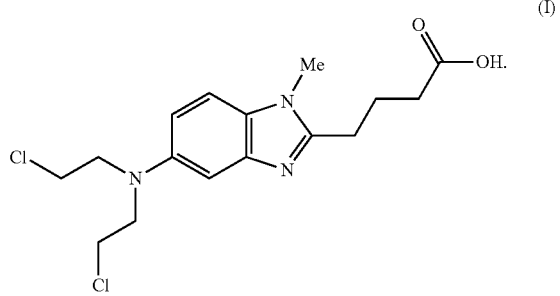 [SMILES: Cn1c(CCCC(=O)O)nc2cc(N(CCCl)CCCl)ccc21]

Bendamustine is used in the treatment of a number of cancers including leukemias, Hodgkins disease and multiple myelomas. Bendamustine is the active ingredient of the commercial product Treanda™, a lyophilized powder for reconstitution.

Bendamustine exhibits rapid degradation upon reconstitution of the lyophilized product. Bendamustine undergoes hydrolysis by direct substitution rather than an addition elimination process due to the presence of the highly labile aliphatic chlorine atoms. Some of the main degradants of bendamustine are the monohydroxy compound known as HP1 (hydrolysis product 1) and dihydroxy compound HP2 (hydrolysis product 2). The monohydroxy compound appears as the main impurity at Relative Retention Time (RRT) 0.6 and the dihydroxy compound appears as the main impurity at RRT 0.27. Minor peaks appear at RRT 1.2, which are presently unknown.

The stability of bendamustine in water is measured in hours, and is therefore, not suitable for long-term storage in liquid form. The lyophile possesses good chemical stability. However, reconstitution of the lyophile is clinically inconvenient, taking 15-30 mins with implications of chemical instability. There is a need for ready to use (RTU) bendamustine formulations having enhanced stability.

SUMMARY OF THE INVENTION

In other aspects of the invention, the bendamustine-containing compositions include a) a pharmaceutically acceptable fluid which contains one or more of propylene glycol, ethanol, polyethylene glycol, benzyl alcohol and glycofurol, and b) a stabilizing amount of a chloride salt. In other aspects of the invention, the bendamustine-containing compositions include DMSO (dimethyl sulfoxide) as part of the pharmaceutically acceptable fluid included therein. Regardless of the pharmaceutically acceptable fluid included, the amount of bendamustine included in the composition is preferably from about 20 mg/mL to about 60 mg/mL. Still further aspects of the invention include methods of treatment using bendamustine-containing compositions and kits containing the same.

One of the advantages of the inventive liquid compositions is that they have substantially improved long term stability when compared to currently available formulations. For example, the inventive bendamustine compositions are substantially free of impurities after at least about 15 months at a temperature of from about 5° C. to about 25° C. The inventive formulations are advantageously ready to use or ready for further dilution. Reconstitution of lyophilized powders is not required.

DETAILED DESCRIPTION OF THE INVENTION

Unless defined otherwise, all technical and scientific terms used herein have the same meaning as is commonly understood by one of ordinary skill in the art to which this invention belongs. In the event that there is a plurality of definitions for a term herein, those in this section prevail unless stated otherwise.

As used herein, RRT is calculated by dividing the retention time of the peak of interest by the retention time of the main peak. Any peak with an RRT<1 elutes before the main peak, and any peak with an RRT>1 elutes after the main peak.

For purposes of the present invention, "substantially free of impurities" shall be understood to include bendamustine-containing compositions in which the amount of total impurities is less than about 5%, as calculated on a normalized peak area response ("PAR") basis as determined by high performance liquid chromatography ("HPLC") at a wavelength of 223 nm, after a period of about 15 months at a temperature of from about 5° C. to about 25° C. The amount of impurities is further calculated as being based upon the original amount bendamustine (or salt thereof) being present in the composition or formulation.

For purposes of the present invention, a pharmaceutically acceptable fluid is a fluid which is suitable for pharmaceutical use.

Preferably, the amount of any individual degradant in the inventive compositions does not exceed 2% PAR as determined by HPLC at a wavelength of 223 nm after storage periods of at least about 15 months at a temperature of from about 5° C. to about 25° C. In some aspects, the amount of time the inventive compositions demonstrate long term storage stability is at least about 18 months and preferably at least about 2 years when stored under the conditions described herein.

In accordance with one aspect of the invention there are provided long term storage stable bendamustine-containing compositions including:
  a) bendamustine or a pharmaceutically acceptable salt thereof; and
  b) a pharmaceutically acceptable fluid including
     i) PEG, PG or mixtures thereof; and
     ii) a stabilizing amount of an antioxidant.

The total impurities in the inventive compositions resulting from the degradation of the bendamustine in the compositions is less than about 5% PAR as determined by HPLC at a wavelength of 223 nm after at least about 15 months at a temperature of from about 5° C. to about 25° C., and thus have long term stability for at least the same period of time or longer. Preferably, the bendamustine-containing compositions demonstrate long term storage stability for at least about 2 years, especially when stored at the lower (refrigerated) temperatures. In one embodiment, the amount of total impurities in the inventive compositions resulting from the degradation of the bendamustine is less than about 3% PAR as determined by HPLC at a wavelength of 223 nm after at least about 2 years at a temperature of from about 5° C. to about 25° C.

In some aspects of the invention, the bendamustine concentration in the inventive compositions is from about 10 mg/mL to about 100 mg/mL, preferably 20 mg/mL to about 60 mg/mL. Preferably the bendamustine concentration in the inventive compositions is from about 25 mg/mL to about 50 mg/mL, and more preferably from about 30 mg/mL to about 50 mg/mL. It will be understood that compositions containing any useful concentration within the ranges, i.e. 10, 20, 25, 30, 35, 40, 45, 50, 55, 60 . . . 100 are contemplated. In other embodiments, the bendamustine concentration in the composition is about 50 mg/mL. In alternative aspects, the amount of bendamustine is outside these ranges but the amounts will be sufficient for single or multiple administrations of dosages generally regarded as effective amounts.

In several embodiments of the invention, pharmaceutically acceptable fluid is non-aqueous and may be, but is not necessarily, a solvent for the bendamustine or salt thereof. Within this aspect, the pharmaceutically acceptable fluid is propylene glycol (PG) or polyethylene glycol (PEG). In other embodiments of the invention however, the pharmaceutically acceptable fluid is a mixture of PEG and PG. For example, the pharmaceutically acceptable fluid can include about 50% PEG and about 50% PG. Alternatively, pharmaceutically acceptable fluid includes about 95% PEG and about 5% PG. The amount of PEG and PG can also be varied within the ranges, i.e. the ratio of PEG:PG in the pharmaceutically acceptable fluid can range from about 95:5 to about 50:50. Within this range, is a pharmaceutically acceptable fluid containing about 75% PEG and about 25% PG, and preferably 80% PEG and 20% PG. In another embodiment, a pharmaceutically acceptable fluid can include about 85% PEG and about 15% PG while another preferred pharmaceutically acceptable fluid includes about 90% PEG and about 10% PG. The molecular weight of the PEG will be within the range of pharmaceutically acceptable weights although PEG 400 is preferred in many aspects of the invention.

Without meaning to be bound by any theory or hypothesis, the hydroxide of the polyethylene glycol molecule is less reactive than the hydroxides of propylene glycol. As a result, the ester forms at a slower rate in polyethylene glycol than propylene glycol and the resulting bendamustine degradants are unexpectedly and substantially reduced over extended periods of time when PEG is a substantial part of the pharmaceutically acceptable fluid.

The bendamustine-containing compositions according to several preferred aspects of the invention include a stabilizing amount of an antioxidant. For purposes of the present invention, "stabilizing amount" shall be understood to include those amounts which increase or enhance the stability of the bendamustine in the compositions described herein. The presence of one or more antioxidants described herein thus contributes, at least in part to the long term stability of the composition. Within this guideline, suitable antioxidant concentrations in the compositions can range from about 2.5 mg/mL to about 35 mg/mL, and preferably from about 5 mg/mL to about 20 mg/mL or from about 10 mg/mL to about 15 mg/mL. In some other embodiments, the concentration of the antioxidant in the bendamustine-containing composition is about 5 mg/mL.

Suitable antioxidants for inclusion include those which are pharmaceutically acceptable for use in human and veterinary formulations although not limited to those currently regarded as safe by any regulatory authority. For example, the antioxidant can be selected from among lipoic acid, thioglycerol (also known as monothioglycerol) and analogs thereof, propyl gallate, methionine, cysteine, metabisulfites, sodium formaldehyde sulfoxylate, phenol-containing aromatic and aliphatic compounds, dihydrolipoic acid and mixtures of the foregoing. Preferably, the antioxidant is thioglycerol, lipoic acid or a mixture thereof. Some particularly preferred embodiments of the invention include thioglycerol.

In view of the foregoing, some preferred long term storage stable bendamustine-containing compositions in accordance with the invention compositions include:

I. a) bendamustine or a pharmaceutically acceptable salt thereof; and
  b) a pharmaceutically acceptable fluid including
    i) polyethylene glycol and propylene glycol; and
    ii) a stabilizing amount of thioglycerol; or
II. a) about 50 mg/mL bendamustine or a pharmaceutically acceptable salt thereof; and
  b) a pharmaceutically acceptable fluid including
    i) about 90% PEG and about 10% PG; and
    ii) about 2.5 mg/mL thioglycerol.

Each of these compositions have the same stability profiles already described, i.e. having less than about 5% total impurities, PAR as determined by HPLC at a wavelength of 223 nm, after at least about 15 months of storage at a temperature of from about 5° C. to about 25° C.

In accordance with other aspects of the invention, there are provided long term storage stable bendamustine-containing compositions, including:

a) bendamustine or a pharmaceutically acceptable salt thereof;
b) a pharmaceutically acceptable fluid including one or more of the following: PG, ethanol, PEG, benzyl alcohol and glycofurol; and
c) a stabilizing amount of a chloride salt.

These compositions also have the low levels of impurities and long term stability mentioned herein. Preferred pharmaceutically acceptable fluids include PG, PEG or ethanol in this embodiment of the invention. Preferably, the PEG is PEG 400. If desired, glycerin and/or 88% (w/w) lactic acid can be added to the pharmaceutically acceptable fluid.

Suitable chloride salts include but are not limited to organic chloride salts, sodium chloride, choline chloride, hydrochloride salts of amino acids and mixtures thereof. Thus, as will be appreciated by those of ordinary skill, one can select from among a number of suitable chloride salts and it is Applicants' intention that the scope of the invention includes all such chloride salts that are capable of being included in bendamustine-containing formulations for extended periods without having a deleterious effect on the drug. In one embodiment of the invention, the chloride salt concentration is from about 10 to about 300 mg/mL. In another embodiment, the chloride salt concentration is from about 50 to about 215 mg/mL. In one preferred embodiment, the chloride salt concentration is about 215 mg/mL.

In accordance with another aspect of the invention, there is provided long term storage stable bendamustine-containing compositions, including:
a) bendamustine or a pharmaceutically acceptable salt thereof; and
b) a pharmaceutically acceptable fluid including DMSO.

These compositions also have the low levels of impurities and long term stability mentioned herein. In some aspects, the bendamustine concentration in these compositions is from about 10 mg/mL to about 100 mg/mL. Preferably, the bendamustine concentration is from about 20 mg/mL to about 50 mg/mL, more preferably from about 25 mg/mL to about 50 mg/mL. In an alternative embodiment, the bendamustine concentration is about 50 mg/mL.

Another embodiment of the invention provides methods of treating cancer in mammals. The methods include administering to a mammal in need thereof an effective amount of one of the bendamustine-containing compositions described herein. Since the active ingredient portion of the inventive composition is an FDA-approved drug, those of ordinary skill will recognize that the doses of bendamustine employed in this aspect of the invention will be similar to those employed in any treatment regimens designed for bendamustine as marketed under the trade name TRE-ANDA. The patient package insert containing dosing information is incorporated herein by reference. The methods of treatment also include administering the inventive formulations for any purpose or physical condition for which bendamustine has been indicated as being useful.

Another embodiment of the invention includes methods of preparing bendamustine-containing compositions described herein. The methods include reconstituting lyophilized bendamustine in a pharmaceutically acceptable fluid containing one of the following:
A) i) PEG, PG or mixtures thereof; and
   ii) a stabilizing amount of an antioxidant;
B) i) one or more of PG, ethanol, PEG, benzyl alcohol and glycofurol; and
   ii) a stabilizing amount of a chloride salt; or
C) DMSO.

The steps are carried out under pharmaceutically acceptable conditions for sterility and manufacturing.

In a further aspect of the invention, there are provided methods of controlling or preventing the formation of impurities in bendamustine-containing compositions during long term storage. The methods include combining an amount of bendamustine or a pharmaceutically acceptable salt thereof with a sufficient amount of a pharmaceutically acceptable fluid containing one of the following:
A) i) PEG, PG or mixtures thereof; and
   ii) a stabilizing amount of an antioxidant;
B) i) one or more of PG, ethanol, PEG, glycofurol and benzyl alcohol; and
   ii) a stabilizing amount of a chloride salt; or
C) DMSO.

Further optional steps in accordance therewith include transferring one or more pharmaceutically acceptable doses of the formulations into a suitable sealable container and storing the sealed container at a temperature of from about 5° C. to about 25° C. As a result of carrying out these steps, it is possible to control or substantially prevent the formation of impurities which otherwise occur with bendamustine-containing compositions during long term storage so that the artisan is provided with bendamustine-containing formulations having less than about 5% total impurities PAR as determined by HPLC at a wavelength of 223 nm, after at least about 15 months of storage at a temperature of from about 5° C. to about 25° C.

The compositions of the present invention can be packaged in any suitable sterile vial or container fit for the sterile storage of a pharmaceutical such as bendamustine. Suitable containers can be glass vials, polypropylene or polyethylene vials or other special purpose containers and be of a size sufficient to hold one or more doses of bendamustine.

A further aspect of the invention includes kits containing lyophilized bendamustine or a pharmaceutically acceptable salt thereof in a first container or vial; and, in a second container, a sufficient amount of a pharmaceutically acceptable fluid such as those described herein, i.e. one of the following:
A) i) PEG, PG or mixtures thereof; and
   ii) a stabilizing amount of an antioxidant;
B) i) one or more of PG, ethanol, PEG, glycofurol and benzyl alcohol; and
   ii) a stabilizing amount of a chloride salt; or
C) DMSO.

For purposes of this embodiment, the amount of fluid which is sufficient is an amount which allows the bendamustine to be dissolved or dispersed to a degree which renders the liquid composition ready for use.

As will be appreciated by those of ordinary skill, the kit will contain other pharmaceutically necessary materials for storing and/or administering the drug, including instructions for storage and use, additional diluents, if desired, etc.

EXAMPLES

The following examples serve to provide further appreciation of the invention but are not meant in any way to restrict the effective scope of the invention.

Example 1

Bendamustine-containing compositions were prepared by dissolving bendamustine HCl to a concentration of 10 mg/ml in one of ethanol, propylene glycol and benzyl alcohol as indicated in Table 1 below. 215 mg/ml of choline chloride was added in half of the samples as a source of soluble chloride ions. The samples were maintained at 40° C. and analyzed periodically for drug content and total impurities. The results obtained are presented in Table 1.

TABLE 1

Stability of Bendamustine HCl

| Formulation | Temp | Time | BDM mg/ml | % Total Impurities |
|---|---|---|---|---|
| BDM - 10 mg/mL | | Initial | 10.43 | 0.27 |
| Choline chloride - | 40° C. | 48 hrs | 10.48 | 1.27 |
| 215 mg/mL | | 7 day | 10.26 | 2.11 |
| Ethanol qs to 1 mL | | | | |
| BDM - 10 mg/mL | | Initial | 10.55 | 0.27 |
| Ethanol qs to 1 mL | 40° C. | 48 hrs | 10.30 | 2.39 |
| | | 7 day | 9.55 | 6.66 |
| BDM - 10 mg/mL | | Initial | 9.99 | 0.21 |
| Choline chloride - | 40° C. | 48 hrs | 9.95 | 0.60 |
| 215 mg/mL | | 7 day | 9.43 | 2.31 |
| Propylene glycol qs | | | | |
| to 1 mL | | | | |
| BDM - 10 mg/mL | | Initial | 9.68 | 0.21 |
| Propylene glycol qs | 40° C. | 48 hrs | 9.45 | 0.88 |
| to 1 mL | | 7 day | 9.00 | 3.44 |
| BDM - 10 mg/mL | | Initial | 9.95 | 1.19 |

TABLE 1-continued

Stability of Bendamustine HCl

| Formulation | Temp | Time | BDM mg/ml | % Total Impurities |
|---|---|---|---|---|
| Choline Chloride - 215 mg/mL Benzyl alcohol qs to 1 mL | 40° C. | 48 hrs | 9.89 | 3.51 |
| | | 7 day | 8.97 | 4.24 |
| BDM - 10 mg/mL Benzyl alcohol qs to 1 mL | | Initial | 9.52 | 0.33 |
| | 40° C. | 48 hrs | 8.67 | 4.18 |
| | | 7 day | 7.49 | 7.84 |

Note:
In Table 1 the total % impurities include total contributions from peaks at various RRTs.

As shown in Table 1, the bendamustine formulations are very stable in solutions containing solvent and chloride salt. Table 1 shows that bendamustine, when dissolved at a concentration of about 10 mg/mL, in a pharmaceutically acceptable fluid, such as ethanol and propylene glycol, and containing a stabilizing amount of a chloride salt, such as choline chloride, had less than about 5% after at least 7 days storage at 40° C.

The data presented in Table 1 translates to bendamustine-containing compositions including a pharmaceutically acceptable fluid and a stabilizing amount of a chloride salt having a shelf life of at least about 15 months at 5° C. and 25° C.

The sample including ethanol alone exhibited more than 6.5 total degradants after 7 days storage at 40° C. The sample including benzyl alcohol alone exhibited more than 7.5% total degradants after 7 days storage at 40° C. Bendamustine-containing compositions with such high levels of degradation would not be suitable for long-term storage.

Example 2

Bendamustine-containing compositions were prepared by dissolving bendamustine HCl to a concentration of 10 mg/ml in DMSO. The samples were maintained at 40° C. and analyzed periodically for drug content and impurity profile. The results obtained are presented in Table 2.

TABLE 2

Stability of Bendamustine HCl in DMSO

| Formulation | Temp | Time | Content (mg/mL) | % Total Imp |
|---|---|---|---|---|
| BDM - 10 mg/mL DMSO qs to 1 mL | | Initial | 10.2 | 0.23 |
| | 40° C. | 48 hrs | 9.80 | 0.30 |
| | | 1 week | 10.0 | 0.56 |

Note:
In Table 2 the total % impurities include total contributions from peaks at various RRTs.

Table 2 shows that bendamustine, when dissolved in DMSO, had substantially no increase in total degradants. The data presented in Table 2 translates to bendamustine-containing compositions including DMSO having a shelf life of at least about 15 months at 5° C. and 25° C. In fact, such compositions are expected to have long term stability for periods beyond 15 months, i.e. up to 2 years or greater.

Example 3

Bendamustine-containing compositions were prepared by dissolving bendamustine HCl to a concentration of 20 mg/ml in polyethylene glycol 400 and 5 mg/ml of lipoic acid was added as a stabilizing antioxidant as indicated in Table 3 below. The samples were maintained at 40° C. or 25° C. and analyzed after 15 days for drug content and impurities. The results obtained are presented in Table 3.

TABLE 3

Stability of Bendamustine (20 mg/ml) in PEG 400 and Antioxidants

| Antioxidant | T° C. | Time days | % Initial | % Imp RRT 0.58 | % Total Imps |
|---|---|---|---|---|---|
| None | 25 | 15 | 97.6 | 2.08 | 2.28 |
| | 40 | 15 | 56.3 | 2.17 | 41.9 |
| Lipoic Acid 5 mg/ml | 25 | 15 | 98.5 | <LD | 0.23 |
| | 40 | 15 | 97.5 | 0.33 | 0.53 |

<LD = Below Level of Detection

As shown in Table 3, bendamustine, when dissolved in a pharmaceutically acceptable fluid, such as polyethylene glycol, in the presence of a stabilizing amount of an antioxidant, such as lipoic acid, had substantially no increase in total degradants after a period of 15 days. The data presented in Table 3 translates to bendamustine-containing compositions including a pharmaceutically acceptable fluid and a stabilizing amount of an antioxidant having a shelf life of at least about 15 months at 5° C. and 25° C.

The sample including PEG alone, on the other hand, which did not contain an antioxidant, did not exhibit stabilizing effects at 40° C. This sample had more than 40% more total impurities than the sample including lipoic acid. Bendamustine-containing compositions with such high levels of total impurities would not be suitable for long-term storage.

Example 4

Bendamustine-containing compositions were prepared by dissolving bendamustine HCl to a concentration of 50 mg/ml in 90% polyethylene glycol 400 and 10% propylene glycol. 5 mg/ml of thioglycerol, α-lipoic acid or dihydrolipoic acid was added as a stabilizing antioxidant as indicated in Table 4 below. The samples were maintained at 40° C. and analyzed after 15 days or one month for drug content and impurity profile as indicated in Table 4 below. The results obtained are presented in Table 4.

TABLE 4

Stability of Bendamustine (50 mg/ml) in 90% PEG 400, 10% Propylene Glycol and Antioxidant

| | | | | | % Impurities RRT | | |
|---|---|---|---|---|---|---|---|
| Antioxidant | T (° C.) | Time | Content (mg/mL) | % Initial | HP1 0.59 | PG ester 1.10 | % Total Imps |
| Thioglycerol | 40 | initial | 48.8 | 100 | <LD | <LD | 0 |
| | 40 | 1 month | 48.5 | 99.4 | 0.06 | 0.20 | 0.71 |
| α-lipoic acid | 40 | initial | 49 | 100 | <LD | <LD | 0 |
| | 40 | 15 days | 48.8 | 99.6 | 0.19 | 0.13 | 0.32 |
| | 40 | 1 month | 48.7 | 99.4 | 0.34 | 0.26 | 0.79 |

TABLE 4-continued

Stability of Bendamustine (50 mg/ml) in 90% PEG 400,
10% Propylene Glycol and Antioxidant

| | | | | | % Impurities RRT | | |
|---|---|---|---|---|---|---|---|
| Antioxidant | T (° C.) | Time | Content (mg/mL) | % Initial | HP1 0.59 | PG ester 1.10 | % Total Imps |
| Dihydrolipoic acid | 40 | initial | 49.3 | 100 | <LD | <LD | 0 |
| | 40 | 1 month | 47.7 | 97.4 | 0.63 | 0.12 | 1.84 |

<LD = Below Level of Detection

As shown in Table 4, bendamustine, when dissolved in a pharmaceutically acceptable fluid, such as a combination of polyethylene glycol and propylene glycol, in the presence of a stabilizing amount of an antioxidant, such as thioglycerol, α-lipoic acid or dihydrolipoic acid, had substantially no increase in total degradants after a period of 1 month. This data supports the position that bendamustine-containing compositions according to the invention have a shelf life of at least about 2 years when stored at temperatures between 5° C. and 25° C.

Example 5

Bendamustine-containing compositions were prepared by dissolving bendamustine HCl to a concentration of 50 mg/ml in a mixture of polyethylene glycol 400 and propylene glycol as indicated in Table 5 below. 5 mg/ml of lipoic acid was added as a stabilizing antioxidant. The samples were maintained at 40° C., 25° C. and 5° C. and analyzed after 1 week, 15 days or one month for drug content and impurity profile as indicated in Table 5 below. The results obtained are presented in Table 5.

As shown in Table 5, bendamustine, when dissolved in certain mixtures of polyethylene glycol and propylene glycol and a stabilizing amount of lipoic acid, had substantially no increase in total degradants after a period of 1 month. The data presented in Table 5 translates to bendamustine-containing compositions having a shelf life of at least about 2 years when stored at temperatures between 5° C. and at 25° C.

Example 6

Bendamustine-containing compositions were prepared by dissolving bendamustine HCl to a concentration of 50 mg/ml in 90% polyethylene glycol 400 and 10% propylene glycol and α-lipoic acid was added as a stabilizing antioxidant as indicated in Table 6 below. The samples were maintained at 40° C., 25° C. and 5° C. and analyzed for drug content and impurity profile as indicated in Table 6 below. The results obtained are presented in Table 6.

TABLE 5

Stability of Bendamustine (50 mg/ml) and Lipoic Acid (5 mg/ml)
in PEG400 and Propylene glycol

| | | | | | % Area of degradants | | | % |
|---|---|---|---|---|---|---|---|---|
| Formulation | Temp. | Time Period | Content (mg/mL) | % of Initial | HP1 0.58 | PG ester 1.10 | PG ester 1.13 | Total Imp. |
| BDM - | | Initial | 49.6 | 100 | BDL | BDL | BDL | 0.18 |
| 50 mg/mL | 40° C. | 1 W | 49.0 | 98.8 | 0.05 | 0.13 | BDL | 0.38 |
| Lipoic acid - | | 15 d | 48.3 | 97.4 | 0.08 | 0.26 | BDL | 0.55 |
| 5 mg/mL | | 1 M | 48.0 | 96.8 | 0.11 | 0.43 | 0.13 | 1.03 |
| PEG | 25° C. | 15 d | 49.6 | 100.0 | BDL | 0.10 | BDL | 0.30 |
| 400:PG | | 1 M | 48.4 | 97.6 | 0.05 | 0.19 | BDL | 0.43 |
| (75:25) qs | 5° C. | 1 M | 49.6 | 100.0 | BDL | 0.07 | BDL | 0.27 |
| to 1 mL | | | | | | | | |
| BDM - | | Initial | 50.2 | 100 | BDL | BDL | BDL | 0.21 |
| 50 mg/mL | 40° C. | 1 W | 49.9 | 99.4 | BDL | 0.15 | BDL | 0.30 |
| Lipoic acid - | | 15 d | 49.1 | 97.8 | 0.06 | 0.35 | BDL | 0.73 |
| 5 mg/mL | | 1 M | 49.0 | 97.6 | 0.09 | 0.90 | 0.25 | 1.82 |
| PEG | 25° C. | 15 d | 49.9 | 99.4 | BDL | 0.12 | BDL | 0.32 |
| 400:PG | | 1 M | 49.7 | 99.0 | BDL | 0.25 | BDL | 0.59 |
| (50:50) qs | 5° C. | 1 M | 50.0 | 99.6 | BDL | 0.11 | BDL | 0.33 |
| to 1 mL | | | | | | | | |
| BDM - | | Initial | 50.8 | 100 | BDL | BDL | BDL | 0.21 |
| 50 mg/mL | 40° C. | 1 W | 50.4 | 99.2 | BDL | 0.11 | BDL | 0.30 |
| Lipoic acid - | | 15 d | 49.7 | 97.8 | 0.07 | 0.17 | BDL | 0.43 |
| 5 mg/mL | | 1 M | 49.7 | 97.8 | 0.13 | 0.27 | 0.09 | 0.84 |
| PEG | 25° C. | 15 d | 50.8 | 100.0 | BDL | 0.10 | BDL | 0.26 |
| 400:PG | | 1 M | 50.8 | 100.0 | 0.05 | 0.14 | BDL | 0.39 |
| (90:10) qs | 5° C. | 1 M | 50.8 | 100.0 | BDL | 0.06 | BDL | 0.34 |
| to 1 mL | | | | | | | | |

BDL = Below Detectable Limit

TABLE 6

Stability of Bendamustine in 90% PEG 400, 10% PG and α-lipoic acid

| Formulation | Temp | Time Per. | Amt. mg/ml | % of Initial | % Area of degradants | | | | | | | | % Total Imp. |
|---|---|---|---|---|---|---|---|---|---|---|---|---|---|
| | | | | | 0.59 | 1.10 | 1.13 | 1.15 | 1.17 | 1.20 | 1.22 | 1.30 | |
| BDM - | Initial | | 51.0 | 100 | 0.20 | 0.06 | <LD | <LD | <LD | <LD | <LD | <LD | 0.26 |
| 50 mg/mL | 40° C. | 1 M | 50.5 | 99.0 | 0.21 | 0.31 | 0.13 | 0.07 | 0.13 | 0.10 | <LD | <LD | 0.95 |
| α-lipoic | | 2 M | 49.7 | 97.5 | 0.22 | 0.71 | 0.28 | 0.14 | 0.12 | 0.21 | 0.12 | <LD | 2.02 |
| acid - | | 3 M | 48.7 | 95.5 | 0.22 | 1.01 | 0.45 | 0.21 | 0.14 | 0.37 | 0.16 | 0.05 | 2.96 |
| 10 mg/mL | 25° C. | 3 M | 50.5 | 99.0 | 0.20 | 0.36 | 0.07 | <LD | <LD | 0.10 | <LD | <LD | 0.73 |
| PEG | | 6 M | 50.4 | 98.8 | 0.22 | 0.60 | 0.17 | 0.06 | 0.06 | 0.09 | 0.10 | 0.08 | 1.44 |
| 400:PG | 5° C. | 6 M | 50.9 | 99.8 | 0.16 | 0.05 | <LD | <LD | <LD | <LD | <LD | <LD | 0.21 |
| (90:10) qs | | 12 M | 50.6 | 99.2 | 0.20 | 0.18 | <LD | <LD | <LD | <LD | <LD | <LD | 0.38 |
| to 1 mL | | | | | | | | | | | | | |
| BDM - | Initial | | 50.3 | 100 | 0.18 | <LD | <LD | <LD | <LD | <LD | <LD | <LD | 0.18 |
| 50 mg/mL | 40° C. | 1 M | 50.0 | 99.4 | 0.19 | 0.32 | 0.08 | 0.06 | 0.08 | 0.06 | 0.06 | <LD | 0.85 |
| α-lipoic | | 2 M | 49.8 | 99.0 | 0.19 | 0.65 | 0.21 | 0.12 | 0.13 | 0.23 | 0.14 | 0.06 | 1.85 |
| acid - | | 3 M | 49.5 | 98.4 | 0.15 | 0.89 | 0.37 | 0.17 | 0.13 | 0.32 | 0.10 | <LD | 2.40 |
| 15 mg/mL | | 6 M | 47.0 | 93.4 | 0.20 | 1.76 | 0.66 | 0.19 | 0.31 | 0.47 | 0.33 | 0.17 | 4.93 |
| PEG | 25° C. | 3 M | 50.0 | 99.4 | 0.20 | 0.35 | 0.08 | <LD | <LD | <LD | 0.11 | <LD | 0.79 |
| 400:PG | | 6 M | 49.5 | 98.4 | 0.19 | 0.58 | 0.15 | 0.06 | 0.07 | 0.09 | 0.08 | 0.10 | 1.38 |
| (90:10) qs | 5° C. | 6 M | 50.3 | 100 | 0.17 | 0.06 | <LD | <LD | <LD | <LD | <LD | <LD | 0.23 |
| to 1 mL | | 12 M | 50.2 | 99.8 | 0.19 | 0.15 | <LD | <LD | <LD | <LD | <LD | <LD | 0.34 |

<LD = Below Level of Detection

The data reported in Table 6 along with the data in Table 5 demonstrates that bendamustine solutions are stable when dissolved in mixtures of PEG and PG and 5-15 mg/mL α-lipoic acid. As shown in Table 6, bendamustine, when dissolved in combinations of polyethylene glycol and propylene glycol, in the presence of a stabilizing amount of lipoic acid, had less than 3% increase in total degradants after a period of 3 months at 40° C. Additionally, the same compounds had substantially no increase in total degradants after a period of 6-12 months at 5° C. and 25° C. The data corresponds to bendamustine solutions being stable under ambient or refrigerated storage conditions for well in excess of 2 years, and thus long term stable.

Example 7

Bendamustine-containing compositions were prepared by dissolving bendamustine HCl to a concentration of 50 mg/ml in 90% polyethylene glycol 400 and 10% propylene glycol. 2.5 mg/ml of thioglycerol was added as an antioxidizing agent. The samples were maintained at 40° C. and 25° C. and analyzed for drug content and impurity profile as indicated in Table 7 below. The results obtained are presented in Table 7.

The stability is similar to that of α-lipoic acid samples in Example 6 above. As shown in Table 7, bendamustine, when dissolved in a combination of polyethylene glycol and propylene glycol, and a stabilizing amount of thioglycerol, had less than 3% increase in total degradants after a period of 3 months at 40° C. Additionally, the same compounds had substantially no increase in total degradants after a period of 6 months at 25° C. The data reported supports the conclusion that these bendamustine solutions are stable under ambient or refrigerated storage conditions for about 2 years.

Example 8

Bendamustine-containing compositions were prepared by dissolving bendamustine HCl to a concentration of 50 mg/ml in 85% PEG 400 and 15% PG in the presence of 5 mg/ml of thioglycerol. The samples were maintained at 40° C. and 25° C. and analyzed for drug content and impurity profile as indicated in Table 8 below. The results obtained are presented in Table 8.

TABLE 7

Stability of Bendamustine in 90% PEG 400, 10% PG and Thioglycerol

| Formulation | Temp | Time Per. | Amt mg/ml | % of Initial | RRTs of degradants | | | | | | | | | % Total Imp. |
|---|---|---|---|---|---|---|---|---|---|---|---|---|---|---|
| | | | | | 0.15 | 0.37 | 1.10 | 1.13 | 1.15 | 1.17 | 1.18 | 1.20 | 1.22 | |
| BDM - | Initial | | 50.3 | 100 | BDL | BDL | BDL | BDL | BDL | BDL | BDL | BDL | BDL | 0.00 |
| 50 mg/mL | 40° C. | 15 d | 50.2 | 99.8 | BDL | BDL | 0.18 | BDL | BDL | BDL | 0.05 | 0.08 | BDL | 0.31 |
| Thio | | 1 M | 49.9 | 99.2 | BDL | 0.12 | 0.32 | 0.07 | BDL | BDL | 0.09 | 0.08 | BDL | 0.75 |
| glycerol - | | 2 M | 49.1 | 97.6 | BDL | 0.18 | 0.56 | 0.24 | 0.09 | 0.17 | 0.19 | 0.12 | 0.11 | 1.76 |
| 2.5 mg/mL | | 3 M | 48.8 | 97.0 | BDL | 0.23 | 0.85 | 0.34 | 0.16 | 0.30 | 0.34 | 0.29 | 0.19 | 2.94 |
| PEG | 25° C. | 3 M | 49.9 | 99.2 | 0.06 | 0.12 | 0.23 | 0.07 | BDL | 0.06 | 0.07 | 0.06 | BDL | 0.67 |
| 400:PG | | 6 M | 49.3 | 98.0 | BDL | 0.23 | 0.53 | 0.22 | 0.11 | BDL | 0.21 | 0.22 | 0.20 | 2.07 |
| (90:10) qs | | | | | | | | | | | | | | |
| to 1 mL | | | | | | | | | | | | | | |

BDL = Below Detectable Limit

TABLE 8

Stability of Bendamustine in 85% PEG 400, 15% PG and Thioglycerol

| Formulation | Temp. | Time Period | Content (mg/mL) | % of Initial | % Total Imp. |
|---|---|---|---|---|---|
| BDM - 50 mg/mL | Initial | | 51.5 | 100 | 0.12 |
| Thioglycerol - | 40° C. | 1 M | 50.4 | 97.9 | 1.18 |
| 5 mg/mL | 25° C. | 1 M | 51.4 | 99.8 | 0.41 |
| PEG 400:PG (85:15) | | 3 M | 50.4 | 97.9 | 1.21 |
| qs to 1 mL | 5° C. | 3 M | 51.0 | 99.0 | 0.26 |

The stability is similar to that of thioglycerol samples in Example 7 above. As reported in Table 8, total impurities did not exceed 2% at 40° C. or 25° C. storage over one month, or at 25° C. and 5° C. storage after three months. The data reported in Table 8 supports the conclusion that these bendamustine solutions are stable under ambient or refrigerated storage conditions for at least about 2 years if not longer.

We claim:

1. A liquid bendamustine-containing composition, comprising:
    a) bendamustine or a pharmaceutically acceptable salt thereof; and
    b) a pharmaceutically acceptable fluid comprising about 5% to about 10% propylene glycol, polyethylene glycol and a stabilizing amount of an antioxidant selected from the group consisting of thioglycerol, monothioglycerol, lipoic acid, propyl gallate, methionine, cysteine, metabisulfites, sodium formaldehyde sulfoxylate, phenol-containing aromatic and aliphatic compounds and dihydrolipoic acid;
    the bendamustine-containing composition having less than or equal to 0.11% total PG esters at about 1 month of storage at a temperature of about 5° C.;
    wherein the ratio of polyethylene glycol to propylene glycol is selected from the group consisting of: about 95:5, about 90:10, about 85:15, about 80:20 and about 75:25.

2. The liquid bendamustine-containing composition of claim 1, wherein said bendamustine-containing composition has less than or equal to 0.18% total PG esters at about 12 months of storage at a temperature of about 5° C.

3. The liquid bendamustine-containing composition of claim 1, wherein the amount of propylene glycol in the pharmaceutically acceptable fluid is about 10%.

4. The liquid bendamustine-containing composition of claim 1, wherein the bendamustine concentration is from about 20 mg/mL to about 60 mg/mL.

5. The liquid bendamustine-containing composition of claim 4, wherein the bendamustine concentration is from about 25 mg/mL to about 50 mg/mL.

6. The liquid bendamustine-containing composition of claim 5, wherein the bendamustine concentration is about 50 mg/mL.

7. A liquid bendamustine-containing composition, comprising:
    a) bendamustine or a pharmaceutically acceptable salt thereof; and
    b) a pharmaceutically acceptable fluid comprising propylene glycol, polyethylene glycol and a stabilizing amount of an antioxidant selected from the group consisting of thioglycerol, monothioglycerol, lipoic acid, propyl gallate, methionine, cysteine, metabisulfites, sodium formaldehyde sulfoxylate, phenol-containing aromatic and aliphatic compounds and dihydrolipoic acid;
    the bendamustine-containing composition having less than or equal to 0.12% total PG esters at about 15 days of storage at a temperature of about 25° C.;
    wherein the ratio of polyethylene glycol to propylene glycol is selected from the group consisting of: about 95:5, about 90:10, about 85:15, about 80:20 and about 75:25.

8. The liquid bendamustine-containing composition of claim 7, wherein said bendamustine-containing composition has less than or equal to 0.25% total PG esters at about 1 month of storage at a temperature of about 25° C.

9. The liquid bendamustine-containing composition of claim 7, wherein said bendamustine-containing composition has less than or equal to 0.43% total PG esters at about 3 months of storage at a temperature of about 25° C.

10. The liquid bendamustine-containing composition of claim 7, wherein said bendamustine-containing composition has less than or equal to 0.77% total PG esters at about 6 months of storage at a temperature of about 25° C.

11. The liquid bendamustine-containing composition of claim 7, wherein the bendamustine-containing composition has less than or equal to 0.25% total PG esters at about 1 month of storage at a temperature of about 25° C., has less than or equal to 0.43% total PG esters at about 3 months of storage at a temperature of about 25° C., and has less than or equal to 0.77% total PG esters at about 6 months of storage at a temperature of about 25° C.

12. The liquid bendamustine-containing composition of claim 7, wherein the amount of propylene glycol in the pharmaceutically acceptable fluid is about 10%.

13. The liquid bendamustine-containing composition of claim 7, wherein the bendamustine concentration is from about 20 mg/mL to about 60 mg/mL.

14. The liquid bendamustine-containing composition of claim 7, wherein the bendamustine concentration is from about 25 mg/mL to about 50 mg/mL.

15. The liquid bendamustine-containing composition of claim 14, wherein the bendamustine concentration is about 50 mg/mL.

16. A liquid bendamustine-containing composition, comprising:
    a) bendamustine or a pharmaceutically acceptable salt thereof; and
    b) a pharmaceutically acceptable fluid comprising about 5% to about 10% propylene glycol, polyethylene glycol and a stabilizing amount of an antioxidant selected from the group consisting of thioglycerol, monothioglycerol, lipoic acid, propyl gallate, methionine, cysteine, metabisulfites, sodium formaldehyde sulfoxylate, phenol-containing aromatic and aliphatic compounds and dihydrolipoic acid;
    wherein the ratio of polyethylene glycol to propylene glycol is selected from the group consisting of: about 95:5, about 90:10, about 85:15, about 80:20 and about 75:25.

17. The liquid bendamustine-containing composition of claim 16, wherein said bendamustine-containing composition has less than or equal to 0.11% total PG esters at about 1 month of storage at a temperature of about 5° C.

18. The liquid bendamustine-containing composition of claim 16, wherein said bendamustine-containing composition has less than or equal to 0.18% total PG esters at about 12 months of storage at a temperature of about 5° C.

19. The liquid bendamustine-containing composition of claim 16, wherein said bendamustine-containing composition has less than or equal to 0.12% total PG esters at about 15 days of storage at a temperature of about 25° C.

20. The liquid bendamustine-containing composition of claim 16, wherein said bendamustine-containing composition has less than or equal to 0.25% total PG esters at about 1 month of storage at a temperature of about 25° C.

21. The liquid bendamustine-containing composition of claim 16, wherein said bendamustine-containing composition has less than or equal to 0.43% total PG esters at about 3 months of storage at a temperature of about 25° C.

22. The liquid bendamustine-containing composition of claim 16, wherein said bendamustine-containing composition has less than or equal to 0.77% total PG esters at about 6 months of storage at a temperature of about 25° C.

23. The liquid bendamustine-containing composition of claim 16, wherein the bendamustine concentration is from about 20 mg/mL to about 60 mg/mL.

24. The liquid bendamustine-containing composition of claim 23, wherein the bendamustine concentration is about 50 mg/mL.

25. The liquid bendamustine-containing composition of claim 16, wherein the antioxidant is thioglycerol or monothioglycerol.

26. The liquid bendamustine-containing composition of claim 16, wherein the antioxidant concentration is from about 2.5 mg/mL to about 35 mg/mL.

\* \* \* \* \*